US010233537B2

(12) United States Patent
Li et al.

(10) Patent No.: US 10,233,537 B2
(45) Date of Patent: Mar. 19, 2019

(54) ARTIFICIAL JOINT CUP, MAGNETIC CONTROL SPUTTERING COATING FILM DEVICE AND PREPARATION METHOD THEREOF

(71) Applicant: Zhongao Huicheng Technology Co., Ltd., Beijing (CN)

(72) Inventors: Lingling Li, Beijing (CN); Gong Jin, Beijing (CN); Jiangping Tu, Beijing (CN)

(73) Assignee: Zhongao Huicheng Technology Co., Ltd., Beijing (CN)

( * ) Notice: Subject to any disclaimer, the term of this patent is extended or adjusted under 35 U.S.C. 154(b) by 106 days.

(21) Appl. No.: 15/120,703

(22) PCT Filed: Apr. 23, 2014

(86) PCT No.: PCT/CN2014/076043
§ 371 (c)(1),
(2) Date: Aug. 22, 2016

(87) PCT Pub. No.: WO2015/161469
PCT Pub. Date: Oct. 29, 2015

(65) Prior Publication Data
US 2017/0029935 A1    Feb. 2, 2017

(51) Int. Cl.
C23C 14/35    (2006.01)
A61L 27/30    (2006.01)
(Continued)

(52) U.S. Cl.
CPC ............. *C23C 14/352* (2013.01); *A61F 2/30* (2013.01); *A61L 27/30* (2013.01);
(Continued)

(58) Field of Classification Search
USPC ............ 623/20.22, 21.13, 21, 22; 204/192.1, 204/192.12, 192.14, 192.15, 192.16,
(Continued)

(56) References Cited

U.S. PATENT DOCUMENTS 5,370,684 A * 12/1994 Vallana ................. A61L 27/303
623/1.26
6,562,445 B2 * 5/2003 Iwamura ............... C23C 28/046
428/336

(Continued)

FOREIGN PATENT DOCUMENTS

CN    101224141 A    7/2008
CN    101418433 A    4/2009
(Continued)

OTHER PUBLICATIONS

Voevodin et al "Design of a Ti/TiC/DLC functionally gradient coating based on studies of structural trasitions in Ti—C thin films" Thin Solid Films 298 (1997) p. 107-115.*
(Continued)

*Primary Examiner* — Archene A Turner
(74) *Attorney, Agent, or Firm* — Sheppard Mullin Richter & Hampton LLP

(57) ABSTRACT

The present invention aims at improving and upgrading the conventional devices based on the low temperature magnetron sputtering coating devices. Starting from the material systems, the invention provides a new material system and a manufacturing method thereof based on a high molecular weight polyethylene joint cup to solve the poor binding force problem between the film and the matrix, and the problems of easy oxidization and carbonization of high molecular weight polyethylene with low temperature magnetron sputtering technologies at the same time. On the above basis, the ultra-lubrication performance of graphite-like structure films and ultra-hardness of diamond-like struc-
(Continued)

ture films are utilized to construct a nano-scale multilayer structure DLC film alternatively coated with a graphite-like film and a diamond-like film. The present invention improves the wear resistance of high molecular weight polyethylene joint cups, and restricts low accuracy of joints due to creeping by constructing a new artificial hip joint cup of ultra-wear-resisting nano-scale multilayer structure DLC film with high hardness and self-lubricating capability.

27 Claims, 3 Drawing Sheets

(51) Int. Cl.
    *A61F 2/30*     (2006.01)
    *C23C 14/06*     (2006.01)
    *C23C 14/20*     (2006.01)
    *C23C 14/50*     (2006.01)
    *H01J 37/34*     (2006.01)

(52) U.S. Cl.
    CPC ...... *C23C 14/0605* (2013.01); *C23C 14/0611* (2013.01); *C23C 14/20* (2013.01); *C23C 14/35* (2013.01); *C23C 14/505* (2013.01); *H01J 37/345* (2013.01); *H01J 37/3429* (2013.01); *A61F 2210/0076* (2013.01); *A61F 2240/001* (2013.01); *A61F 2310/00389* (2013.01); *A61F 2310/00407* (2013.01)

(58) Field of Classification Search
    USPC .......... 204/298.01, 298.02, 298.04; 428/336, 428/408, 698
    See application file for complete search history.

(56) References Cited

U.S. PATENT DOCUMENTS

| | | | | |
|---|---|---|---|---|
| 6,740,393 | B1 * | 5/2004 | Massler | ................ C23C 16/029 |
| | | | | 428/698 |
| 6,800,095 | B1 * | 10/2004 | Pope | ................... A61F 2/30767 |
| | | | | 428/212 |
| 7,820,293 | B2 * | 10/2010 | Dekempeneer | ....... C23C 28/044 |
| | | | | 428/408 |
| 2007/0111003 | A1 | 5/2007 | Chen | |
| 2013/0309486 | A1 * | 11/2013 | Jin | ........................ C23C 14/025 |
| | | | | 204/192.12 |

FOREIGN PATENT DOCUMENTS

| | | | |
|---|---|---|---|
| CN | 101519769 A | | 9/2009 |
| CN | 101636186 A | | 1/2010 |
| CN | 101681816 A | | 3/2010 |
| CN | 101804708 A | | 8/2010 |
| CN | 102245799 A | | 11/2011 |
| CN | 102247620 A | | 11/2011 |
| CN | 102677009 A | | 9/2012 |
| JP | 11-100671 | * | 4/1999 |
| JP | 2002-322555 | * | 11/2002 |
| JP | 2008-081630 | * | 4/2008 |

OTHER PUBLICATIONS

International Search Report for Application No. PCT/CN2014/076043, dated Jan. 28, 2015, 3 pages. (English Version).

International Search Report and Written Opinion for Application No. PCT/CN2014/076043, dated Jan. 28, 2015, 12 pages. (Chinese Version).

* cited by examiner

ARTIFICIAL JOINT CUP, MAGNETIC CONTROL SPUTTERING COATING FILM DEVICE AND PREPARATION METHOD THEREOF

CROSS-REFERENCE TO RELATED APPLICATIONS

This application is a national stage application of International Application No. PCT/CN2014/076043, filed on Apr. 23, 2014, which is incorporated herein by reference in its entirety.

TECHNICAL FIELD

The present invention relates to the field of materials and medical devices, and particularly to an artificial joint cup product coated with a nano-scale multilayer carbon film, a magnetron sputtering coating device for manufacturing the artificial joint cup and a manufacturing method thereof.

BACKGROUND OF THE INVENTION

With relatively superior physical, chemical and mechanical properties, high molecular weight polyethylene is often used for making artificial joint cups. However, as shown from clinical observations and experiment researches through many years, when matched with metal caput femoris, a high molecular weight polyethylene joint cup has relatively low hardness. In particular, after bearing a large load for long time, the high molecular weight polyethylene joint cup may generate wear-off particles, which may cause bone lysis on some surfaces of the bone joint, and then result in prostheses loosening and shortened service life of the artificial joint cup, thereby increasing clinical risks for a patient in receiving artificial joint revision surgery for second and third times.

In recent years, a matching mode of the same material, such as "ceramic-ceramic" or "gold-gold", has been tried in artificial hip joint prosthesis so as to solve boundary wearing problems between different materials. However, clinical trials have shown that there are still defects in "ceramic-ceramic" or "gold-gold" matching. For example, "ceramic-ceramic" joints are fragile, which limits the activity level and range of the postoperative patients; "gold-gold" joints have significant requirements on surgery condition and physicians' surgery skills; and a slight deviation in a joint replacement may accelerate wearing at joint edges and then generate large quantities of chippings and abnormal noises. Therefore, for artificial hip joints, the majority products still use the matching mode of a high molecular weight polyethylene joint cup and metal ball.

High molecular weight polyethylene wearing is mainly affected by material performance and the processing procedure. Researches have used crosslinking modification and physical modification to improve wear resistance of high molecular weight polyethylene. For regarding radiation crosslinking modification, there are oxidation and catalysis problems for high molecular weight polyethylene; for ion injection crosslinking modification, limited ion injection depth (at 50~100 keV injection energy, layer thickness is about 0.1~0.2 μm) cannot meet requirements on a medical high molecular weight polyethylene material; the physical filling mode improves the wear resistance, but it reduces the tensile strength, shock-absorbing strength, elongation at break and other important mechanical properties. Therefore, the above mode is mainly applied to industrial fields at present.

Through a coating technology, additional properties may be added to a substrate material. Researches have tried to coat a diamond-like carbon film over a surface of high molecular weight polyethylene joint cups to improve the wear resistance of a high molecular weight polyethylene material while guaranteeing the properties of the high molecular weight polyethylene material at the same time. However, as a soft material, high molecular weight polyethylene has poor heat resisting property, and is readily to be carbonizable and oxidizable; therefore, to deposit a coating on the material, there are high requirements on the coating processes and equipment. As how to realize coating on a high molecular weight polyethylene surface under nondestructive conditions, there are extremely high requirements on the design of coating material system, process requirement and equipment performance. At present, there is still no similar product in the market.

The applicant's prior invention with the publication number of 201210151152.2 has disclosed a magnetron sputtering coating device, a nano-scale multilayer film and a manufacturing method thereof. In that application, a special sputtering device and sputtering technology are adopted to perform a technology of coating a carbon film in a nano-scale multilayer structure on an artificial joint or the like with high molecular weight polyethylene as a matrix. The matrix comprises a TiC and graphite-like transition layer, a multilayer structure with alternative laminating of graphite-like layers and diamond-like carbon layers, and a top film structure of diamond-like carbon. Based on the material system, the technical solution has considered poor heat resisting property, readily carbonizable and oxidizable properties, readily dissociative and crosslinking properties of the main chain or the side chain of high molecular weight polyethylene, and intends to construct a new material system and a manufacturing method thereof on a high molecular weight polyethylene joint cup surface to solve a poor binding force problem between the film and the matrix, while solving the easy oxidization and carbonization problems of high molecular weight polyethylene with a low temperature magnetron sputtering technology.

Through research and practice, the applicant has improved the shortcomings of the technical solution as discussed above, and has developed improvement plans regarding the device and method for manufacturing the product.

SUMMARY

The present invention is intended to solve at least one of above technical defects and improve the service life of an artificial joint prosthesis.

The embodiments of the present invention are achieved through the following technical solutions:

An artificial joint cup is provided, which comprises a matrix and a nano-scale multilayer film coated on the matrix. The nano-scale multilayer film comprises: a pure Ti bottom layer crosslinked with the matrix, a Ti-TiC transition layer on the pure Ti bottom layer, a composite layer on the Ti-TiC transition layer, and a pure carbon film layer on the composite layer. The composite layer is a nano-scale multilayer structure consisting of a monolayer graphite-like film and a monolayer diamond-like film deposited alternately; in the direction from the bottom layer to the composite layer, the mass percentage of Ti in the Ti-TiC transition layer gradually decreases, and the mass percentage of C therein gradually increases.

Further, the matrix is a high molecular weight polyethylene joint cup.

Further, the binding force between the matrix and the nano-scale multilayer film is greater than 60N.

Further, a hardness of the nano-scale multilayer film is greater than 20 Gpa.

Further, a thickness of the pure Ti bottom layer is 100-300 nm.

Further, a thickness of the Ti-TiC transition layer is 300-500 nm.

Further, the nano-scale multilayer structure of the composite layer may include a monolayer graphite-like film and monolayer diamond-like film deposited alternately.
The monolayer film has a thickness of 10-25 nm and the composite layer has a total thickness of 1.5-5.0 um.

Further, a thickness of the pure carbon film is 100 nm-200 nm.

An embodiment of the present invention further provides a device for manufacturing the above-described artificial joint cup, the device being configured to coat a nano-scale multilayer film on a matrix. The device comprises: a vacuum coating chamber, a sputtering target, a rotary table on a base of the vacuum coating chamber, a work rest on the rotary table, and a first rotational system driving the rotary table to rotate along a center axis of the rotary table. The sputtering target is arranged around the rotary table and vertical to the rotary table; the sputtering target comprises two first sputtering targets and one second sputtering target; the sputtering targets are positioned on a circumference homocentric with the rotary table; the arc between two the first sputtering targets is 180-240°; the second sputtering target halves the arc; the rotary table is fixedly provided with a partition passing the rotary table surface; in a direction vertical to the rotary table, both ends of the partition extends beyond the both ends of the sputtering targets respectively; and the bottom of the first sputtering target is provided with a magnetic field shielding layer.

Further, the first sputtering targets are graphite targets and the second sputtering target is a Ti target or a Ta target.

Further, the magnetic field shielding layer is a silicon steel gasket.

Further, the partition passes the rotary table along a diameter of the rotary table, and the width of the partition is greater than the diameter of the rotary table.

Further, the space between the partition and the circumference at which the sputtering targets is located is 2-10 cm.

Further, the sputtering targets are rectangular.

Further, the partition is made from titanium, aluminum, stainless steel or a combination thereof.

Further, the device also comprises: a second rotational system driving the rotary table to rotate along the center axis of a work rest.

Further, the work rest is arranged on the rotary table via a support lever, and several work rests are arranged on the same support lever with intervals.

Further, the sputtering target is arranged on the inner wall of the vacuum coating chamber.

Further, the arc between two the first sputtering targets is 180°, the sputtering target further comprises another second sputtering target; the two second sputtering targets are arranged oppositely; and the another second sputtering target is in an idle state.

An embodiment of the present invention further provides an method for manufacturing an artificial joint cup with the above device for manufacturing an artificial joint cup, the method being configured to coat a nano-scale multilayer film on the matrix and maintain the rotary table at uniform rotation, and comprising the following steps:

step 1): adjusting an initial magnetic field intensity G1 with the magnetic field shielding layer so as to meet non-destructive sputtering demands on a surface of the high molecular weight polyethylene joint cup;

step 2): controlling an initial operating air pressure of the film coating chamber at P1, and filling in 99.9% argon to clean the target materials and the matrix;

step 3): controlling an operating air pressure of the film coating chamber at P2, and controlling an operating magnetic field intensity of a first sputtering target at G2; coating a pure Ti bottom layer on the matrix using the second sputtering target at an initial current I1 and a bias voltage V1, and performing sputtering for a first predetermined duration;

step 4): maintaining the bias voltage of the second sputtering target; starting from the initial current I1, decreasing the operating current of the second sputtering target by $\Delta I1$ at a time interval T1 until the operating current becomes a first predetermined current value; at the same time, starting from an initial current I2, applying a bias voltage value V2 to the first sputtering target; for each second time interval T2, increasing the operating current of the first sputtering target by $\Delta I2$ until the operating current becomes a second predetermined current value; maintaining the operating voltage of the first sputtering target and the second sputtering target, and performing sputtering for a second predetermined time duration;

step 5): maintaining the operating current of the second sputtering target at the first predetermined current value, or setting and maintaining the operating current of the second sputtering target at a third predetermined current value; maintaining the operating current of the first sputtering target at the second predetermined current value or setting and maintaining the operating current of the first sputtering target at a fourth predetermined current value; maintaining the operating voltage of the first sputtering target and the second sputtering target, and performing sputtering for a third predetermined duration;

step 6): setting the operating current of the second sputtering target as zero; maintaining the operating current of the first sputtering target at the operating current of step 3), or setting and maintaining the operating current of the first sputtering target at a fifth predetermined current value, and performing sputtering for a fourth predetermined duration.

Optionally, the initial magnetic field intensity G1 is 20-30 Gs; the initial operating air pressure P1 is 1.0 mPa; the operating air pressure P2 is controlled at 130 mPa-250 mPa; the operating magnetic field intensity G2 is 10-150 mT; the initial current I1 of the second sputtering target is 3.0-5.0 A; the bias voltage V1 is 90-150V; the $\Delta I1$ is 0.5-1.0 A; the first predetermined current value is 0; the initial operating current I2 is 0; the $\Delta I2$ is 0.5-1.0 A; the second predetermined current value is 3.0-6.0 A; the bias voltage V2 is 60-100V; and the first interval T1 is 3-10 min; the second interval T2 is 3-10 min.

Further, the first predetermined duration is 10-30 min.
Further, the second predetermined duration is 10-30 min.
Further, the third predetermined duration is 5-10 h.
Further, the fourth predetermined duration is 10-20 min.
Further, the temperature during the whole film coating process is controlled at 30-40° C.

Embodiments of the present invention intend to improve and upgrade the present devices based on the low temperature magnetron sputtering coating device. Starting from the material system, the embodiments have considered the poor heat resisting property, easy carbonization and oxidization properties, readily dissociative and crosslinking properties of the main chain or the side chain of high molecular weight polyethylene, and intend to construct a new material system and a manufacturing method thereof on a high molecular weight polyethylene joint cup. The method uses Ti as the matrix and crosslink with high molecular weight polyethylene, and uses the gradient change of proportion between Ti and C to solve the problem of poor binding force between the film and the matrix. At the same time, easy carbonization and oxidization problems of high molecular weight polyethylene are solved with low temperature magnetron sputtering technologies.

On the above basis, ultra-lubricating property of graphite-like structure film and ultra-hardness of diamond-like structure film are utilized to construct a nano-scale multilayer structure DLC film alternatively coated with a graphite-like film and a diamond-like film.

Embodiments of the present invention improve the wear resistance of high molecular weight polyethylene joint cups, and restrict low accuracy of joints due to creeping by constructing a new artificial hip joint cup of ultra-wear-resisting nano-scale multilayer structure DLC film with high hardness and self-lubricating capability.

DETAILED DESCRIPTION

Embodiments of the present invention are described in detail as below, and examples of the embodiments are shown in accompanied drawings, wherein a same or similar number from beginning to end indicates a same or similar element or elements with same or similar function. Embodiments described through reference drawings below are exemplary, only for interpreting the invention, but not limiting the invention.

An artificial joint cup provided in one embodiment of the present invention comprises a matrix and a nano-scale multi-layer film coated on the matrix; in the embodiments of the present invention, the matrix may be an apparatus (such as a bone joint head, a joint cup, etc.) that can be implanted into a human body, or other matrixes, such as an engineering prop, etc.; the matrixes may be made of metal, alloy materials or other materials; the matrix in the present embodiments is high molecular weight polyethylene joint cup.

The nano-scale multi-layer film comprises a pure Ti bottom layer crosslinked with the matrix, a Ti-TiC transition layer on the pure Ti bottom layer, a composite layer on the Ti-TiC transition layer and a pure carbon film layer on the composite layer. The composite layer is a nano-scale multilayer structure including a graphite-like and diamond-like monolayer film deposited alternately. In the direction from the bottom layer to the composite layer, the mass percentage of Ti in the Ti-TiC transition layer gradually decreases, and the mass percentage of C in the Ti-TiC transition layer gradually increases to guarantee better binding force with the bottom layer, decrease permeation of Ti on the bottom to the transition layer. At the same time, with low internal stress and good lubrication property, the lubrication property of the transition layer is improved via the pure top carbon film layer. The binding force between the matrix and nano-scale multi-layer film is greater than 60N and hardness of the nano-scale multi-layer film is greater than 20 Gpa.

Figure 3:
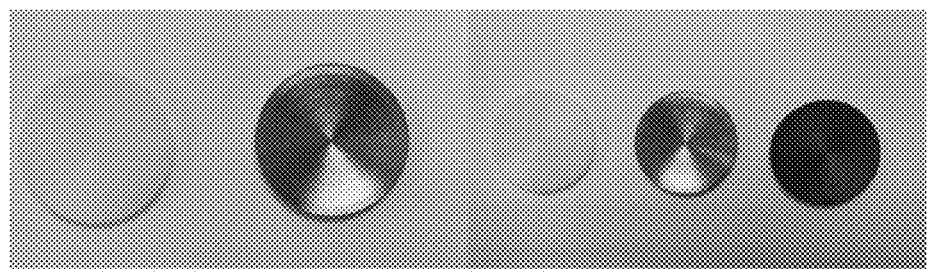
FIG. 3 shows high molecular weight polyethylene coated with a Ti bottom layer and a nano-scale multilayer carbon film.
Figure 4:
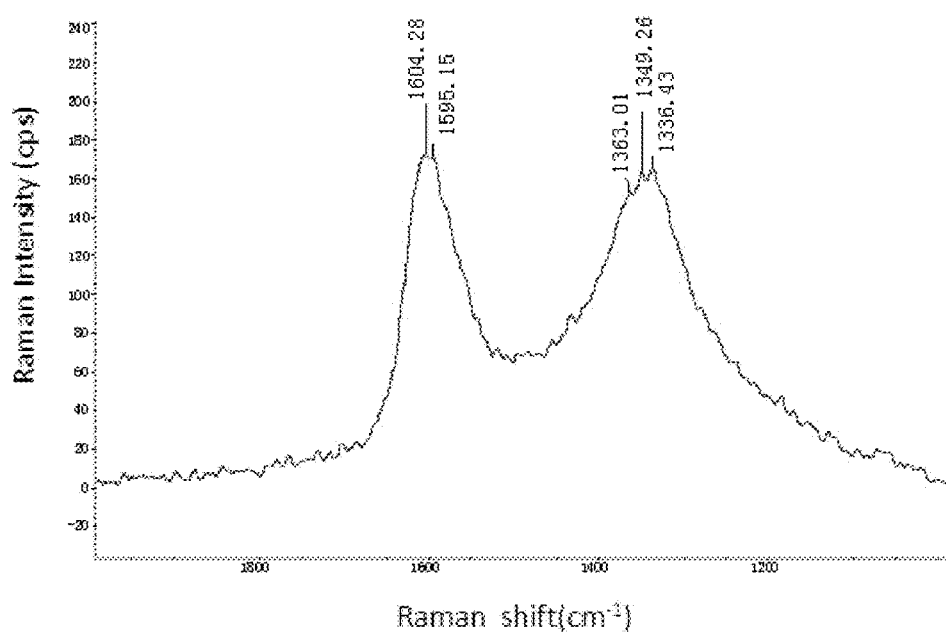
FIG. 4 shows a Raman spectrum of high molecular weight polyethylene coated with nano-scale multilayer carbon film.

FIG. 3 shows high molecular weight polyethylene coated with Ti bottom layer and nano-scale multilayer carbon film. It can be observed from FIG. 3 that after coating with Ti bottom layer, the high molecular weight polyethylene surface has metal luster without the carbonization phenomenon; coated with the carbon film of nano-scale multi-layer structure, the high molecular weight polyethylene surface has gloss black color. FIG. 4 is a Raman spectrum of high molecular weight polyethylene coated with nano-scale multilayer carbon film; through the Raman spectrum of FIG. 4, a carbon film sample in nano-scale multilayer structure of high molecular weight polyethylene coating film is analyzed, and it is learned that at 1,349 $cm^-$ and 1,596 cm, there is a graphite-like (sp2) and diamond-like characteristic peak.

In the embodiments of the present invention, the Ti-TiC transition layer means that the transition layer is the film layer mixed with Ti and TiC. In one embodiment, the transition layer is mixed with Ti and TiC.

In the embodiments of present invention, the layer number of the nano-scale multilayer structure includes a graphite-like and diamond-like monolayer film deposited alternately.

Figure 1:
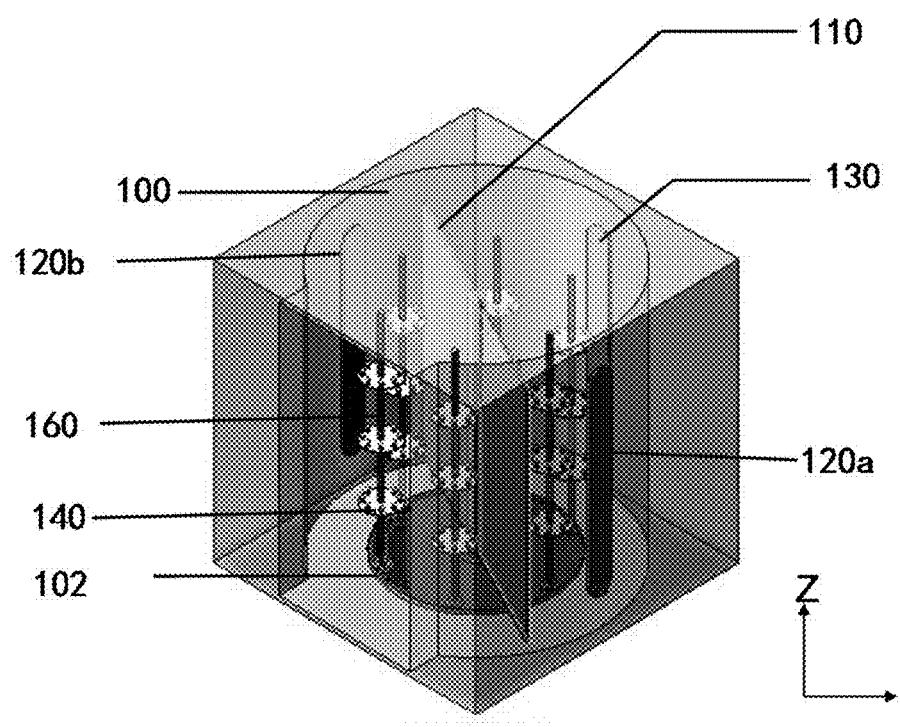
FIG. 1 is a three-dimensional schematic view of a magnetron sputtering coating device according to an embodiment of the present invention.
Figure 2:
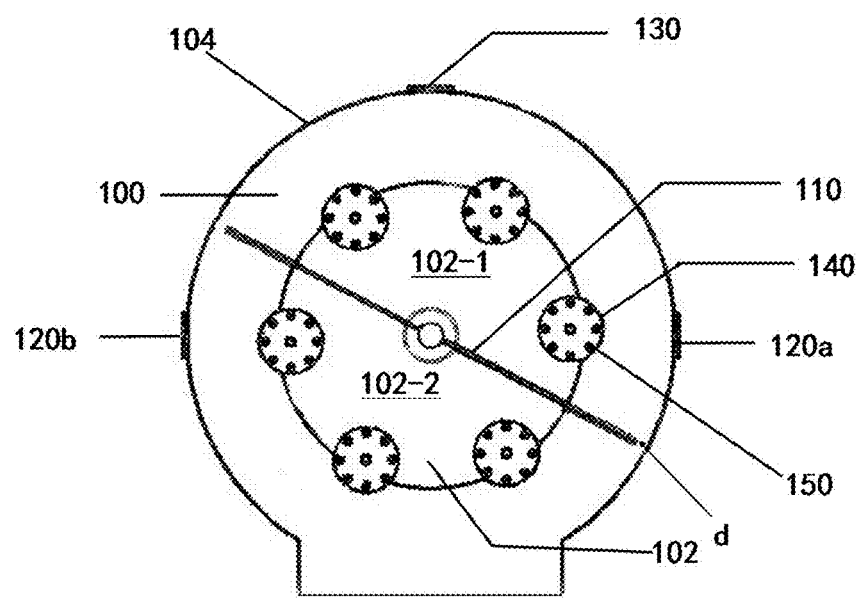
FIG. 2 is a top schematic view of a magnetron sputtering coating device according to FIG. 1.

As shown in FIG. 1 and FIG. 2, one embodiment of the present invention further discloses a device for manufacturing an artificial joint cup, which is configured to coat a nano-scale multilayer film on the matrix. In one embodiment, the device for manufacturing an artificial joint cup is a magnetron sputtering coating device, comprising a vacuum coating chamber, sputtering targets, a rotary table on a base of the vacuum coating chamber, a work rest on the rotary table, and a first rotational system driving the rotary table to rotate along a center axis of the rotary table, and a temperature control system. The device may also include other components, such as a heating device, a cooling water circulating system, a power system connected with the sputtering targets, etc. (not shown in the drawings). The sputtering targets are arranged around the rotary table and vertical to the rotary table; the sputtering target comprises two first sputtering targets and one second sputtering target; the sputtering targets are positioned on a circumference homocentric with the rotary table; the circumference where the sputtering target is located may be a real part, such as the inner wall of the vacuum coating chamber 100, or a suppositional circumference, such as any position between the rotary table and vacuum coating chamber. Two first sputtering targets 120a and 120b are arranged in parallel directions and to halve the circumference 104; the second sputtering target 130 halves the arc between two first sputtering targets 120a and 120b; that is, the arc between the two first sputtering targets 120a and 120b is about 180°, the arc between the second sputtering target 130 and the first sputtering targets 120a and 120b is about 90°, the first sputtering targets 120a and 120b may be the sputtering targets of a certain element; the second sputtering target may be the sputtering target of another element; the sputtering targets material may be selected based on a specific product to be sputtered. For example, in the embodiment, the first sputtering targets are graphite targets, the second sputtering target is a titanium target; in other embodiments, and the first sputtering targets may be carbon targets and the second sputtering target may also be a tantalum target, etc.

In other embodiments, the two first sputtering targets and one second sputtering target can also be arranged with intervals at other angles along a circumference; for example, the radian of the arc between two first sputtering targets 120a and 120b may be other angles between 180° and 240°; whereas, one second sputtering target halves the arc. In this way, the radian of the arc between the second sputtering target and the first sputtering targets may be between 90° and 120°, and the radian of the arc between the second sputtering target 130 and the first sputtering targets 120a and 120b may be 120°.

In the present embodiment, the rotary table 102 is a round table; on the rotary table 102, a partition 110 is fixedly arranged. Preferably, the partition 110 is a straight panel; the partition can be made of titanium, aluminum, stainless steel or combination of these materials; the partition 110 passing through a diameter of the rotary table is vertically arranged on the rotary table 102. Via the partition 110, the rotary table 102 is divided into two mutually independent areas 102-1 and 102-2; along the direction vertical to the rotary table, both ends of the partition 110 extends beyond both ends of sputtering targets 120a, 120b and 130 respectively. In this way, the partition blocks a sputtering target at the other side of a certain area so that the area only receive the coating film of the sputtering target opposite to the area. More preferably, in order to achieve a better blocking effect, a width of the partition is greater than the diameter of the rotary table; wherein, the width means the length of the partition passing through the diameter direction of the rotary table. More preferably, the distance d between the partition and the circumference where the sputtering target is located is 2-10 cm.

The rotary table 102 is provided with a first rotational system (not shown in the drawings) driving the rotary table to rotate along its center axis, namely the rotary table and the partition rotate together along the center axis of the rotary table. When three sputtering targets are at the above-arranged positions, when the rotary table rotates to any position, blocked by the partition 102, one area 102-1 of the rotary table is opposite to the first sputtering target 120a (such as a graphite target) and a second sputtering target 130 (such as a titanium target). Consequently, the product (or a matrix) to be coated in the area 102-1 can be coated with titanium or diamond-like carbon: TiC film (the film layer mixed with Ti and TiC). However, the other area 102-2 of the rotary table is opposite to the first sputtering target 120b (a graphite target), so a product on the area 102-2 is coated with a carbon film. With rotation of the rotary table, products in different areas are coated with titanium or diamond-like carbon in lamination: TiC film and carbon film so as to achieve coating of nano-scale multi-layer film on products. By adjusting rotation speed of the rotary table, thickness of monolayer film can be controlled. The device with simple structure and simple process control solves preparation of multilayer film, thereby being applicable to industrialization.

In other embodiments, the partition 110 may also be vertically arranged at other positions of the rotary table, may also be a bent panel or any other partitions that can divide the rotary table into two mutually independent areas.

In the present embodiment, the device is further provided with a second rotation system driving the rotary table to rotate along the center axis of a work rest; namely, the work rest can rotate on its axis; via the support lever 160, a plurality of work rests 140 can be arranged on the rotary table 102; on same support lever 160, a plurality of work rests 140 can be arranged in a distance to improve the processing efficiency; the work rests 140 are configured to put matrixes (or products) 150 to be processed; products 150 can be evenly arranged on the circumference of the work rests 140. Through rotation of the work rests on their own axes, the film layer coated on a product to be coated with a film on each work rest may possess good evenness.

The above describes the magnetron sputtering coating device of preferred embodiments of the invention. In another preferred embodiment, there are four the sputtering targets (not shown in the drawing) provided around the rotary table. That is to say, the sputtering targets comprise two first sputtering targets and two second sputtering targets; two first sputtering targets are arranged in opposite direction and two second sputtering targets are arranged in opposite direction; four sputtering targets divide the circumference equally. However, during preparation of the multi-layer film, one second target therein does not work. That is to say, corresponding target current, voltage and other parameters are set for two first sputtering targets and one second sputtering target for target sputtering film coating, the other second sputtering target does not perform target sputtering film coating, but being left unused. In the embodiment, although four sputtering targets are arranged, one sputtering target therein does not perform sputtering film coating.

In some embodiments of the present disclosure, a magnetic shielding layer is provided at bottom of the first sputtering target. In one embodiment, utilizing magnetic shielding effect of silicon steel, two pieces of silicon steel sheets in 5 mm thickness and three layers of heat conducting film may be added; two pure graphite targets and one pure Ti target are arranged vertical to the horizontal surface and alternatively in 120° angle. Magnetic field strength is adjusted to achieve nondestructive sputtering demands on f high molecular weight polyethylene and other polymers in accordance with surface oxidization and carbonization generation condition of high molecular weight polyethylene and other polymers.

The magnetron sputtering coating device according to embodiments of the present disclosure is described in detail above. During preparation, various process parameters are set and nano-scale multilayer film is prepared based on specific demands. Therefore, embodiments of the present disclosure further provide a method for coating a film on a matrix based on any of the above magnetron sputtering coating device. The method comprises:

step 1): adjusting an initial magnetic field intensity G1 with the magnetic field shielding layer so as to meet nondestructive sputtering demands on a surface of the high molecular weight polyethylene joint cup;

step 2): controlling an initial operating air pressure of the film coating chamber at P1, and filling in 99.9% argon to clean the target materials and the matrix;

step 3): controlling an operating air pressure of the film coating chamber at P2, and controlling an operating magnetic field intensity of a first sputtering target at G2; coating a pure Ti bottom layer on the matrix using the second sputtering target at an initial current I1 and a bias voltage V1, and performing sputtering for a first predetermined duration;

step 4): maintaining the bias voltage of the second sputtering target; beginning from the initial current I1, decreasing the operating current of the second sputtering target by ΔI1 at a time interval T1 until the operating current becomes a first predetermined current value; at the same time, beginning from an initial current I2, applying a bias voltage value V2 to the first sputtering target; for each second time interval T2, increasing the operating current of the first sputtering target by ΔI2 until the operating current becomes a second predetermined current value; maintaining the operating voltage of the first sputtering target and the second sputtering target, and performing sputtering for a second predetermined time duration;

step 5): maintaining the operating current of the second sputtering target at the first predetermined current value, or setting and maintaining the operating current of the second sputtering target at a third predetermined current value; maintaining the operating current of the first sputtering target at the second predetermined current value or setting and maintaining the operating current of the first sputtering targets at a fourth predetermined current value; maintaining the operating voltage of the first sputtering target and the second sputtering target, and performing sputtering for a third predetermined duration;

step 6): setting the operating current of the second sputtering target as zero; maintaining the operating current of the first sputtering target at the operating current of step 3), or setting and maintaining the operating current of the first sputtering target at a fifth predetermined current value, and performing sputtering for a fourth predetermined duration.

In the embodiments for the manufacturing method of the present invention, three sputtering targets may operate, namely two first sputtering targets and one second sputtering target operate; in the embodiment comprising one other second sputtering target, the second sputtering target is at idling status and does not perform sputtering all the time in preparation of a nano-scale multilayer film.

In some embodiments, the first sputtering targets of the magnetron sputtering coating device are graphite targets and the second sputtering target(s) thereof is a titanium target/are titanium targets; a matrix to be coated (or a product to be coated) is placed on a work rest of a vacuum coating chamber, a high molecular weight polyethylene joint cup is cleaned for 5 min with 99% alcohol and ultrasonic wave, the cup is further cleaned with ultra-pure water and ultrasonic wave for 5 min and then dry the cup with cold air.

At the same time, the initial magnetic field intensity is adjusted to 20-30 Gs with a silicon steel gasket to achieve nondestructive sputtering demands on surface of the high molecular weight polyethylene joint cup; the vacuum coating chamber is vacuumed to 1.0 mPa and then filled in 99.9% argon to clean the target material and the matrix.

After that, sputtering is performed. During the whole sputtering process, the rotary table rotates at a constant speed and the matrix to be coated may also rotate on its axis.

Specifically, the operating air pressure of the coating chamber is controlled and maintained at 130 mPa-250 mPa, magnetic field intensity of the first sputtering targets (such as graphite targets) is 10-150 mT; current of the second sputtering target(s) is 2.0-5.0 A, the bias voltage is 90-150V, pure Ti bottom layer is coated on the matrix for 10-30 min at 100-300 nm thickness.

Afterwards, the current of the second sputtering target(s) is gradually decreased from 3.0-5.0 A at 0.5-1.0 A gradient change to 0.5-1.0 A for 5 times; at the same time, current of two first sputtering targets (graphite targets) is increased at 0.5-1.0 A gradient change from 0 to 3.0-6.0 A for 6 times, that is to say, current of the second sputtering target (s) is at gradient decrease and current of the first sputtering targets is at gradient increase; the increase and decrease amplification may be different or same, and the time interval may also be different or same. During the whole process, the target voltage maintains unchanged at 60-100V bias voltage, coat Ti and TiC gradient film for 10-30 min with 300-500 nm thickness.

Afterwards, while maintaining the currents and bias voltages of the second sputtering target and two first sputtering targets unchanged, on a transition layer, a nano-scale multilayer carbon film is coated, including a graphite-like and diamond-like monolayer film deposited alternately; a thickness of monolayer film is 10-25 nm, a total thickness thereof is 1.5-5.0 um and a total duration is 5-10 h. Current of the second sputtering target is set as 0, further a pure carbon film on the multilayer film structure is deposited for 10-20 min; a thickness of the pure carbon film is 10 nm-200 nm. Thus, a total thickness of the nano-scale multilayer carbon film is 2.0-6.0 μm. During the whole coating process, the temperature is controlled at 30-40° C.

First Embodiment

Two first sputtering targets of a magnetron sputtering coating device are graphite targets and one second sputtering target thereof is a titanium target, the radian between the second sputtering target and the first sputtering target in the sputtering device is basically at 90°, a rotary table rotates at 1.5 rpm and the matrix to be coated rotates on its axis. Before coating, firstly a matrix to be coated (or a product to be coated) is placed on a work rest of a vacuum coating chamber, a high molecular weight polyethylene joint cup is cleaned for 5 min with 99% alcohol and ultrasonic wave, the cup is further cleaned with ultra-pure water and ultrasonic wave for 5 min and then dry the cup with cold air.

At the same time, the initial magnetic field intensity is adjusted at 20 Gs with a silicon steel gasket to achieve nondestructive sputtering demands on surface of the high molecular weight polyethylene joint cup; the vacuum coating chamber is vacuumed to 1.0 mPa and then filled in 99.9% argon to clean the target material and the matrix for 5 min.

After that, sputtering is performed. During the whole sputtering process, the rotary table rotates at a constant speed and the matrix to be coated may also rotate on its axis.

Specifically, the operating air pressure of the coating chamber is controlled and maintained at 150 mPa. The magnetic field intensity of the first sputtering targets (such as graphite targets) is 80 mT; the current of the second sputtering target(s) is 3.0 A, the bias voltage is 90V. Pure Ti bottom layer is coated on the matrix for 10 min with 150 nm thickness.

Afterwards, current of the second sputtering target is gradually decreased from 3.0 A at 0.5 A gradient change to 0.5 A for 5 times; at the same time, current of two first sputtering targets (graphite targets) is increased at 0.5 A gradient change from 0 to 3.0 A for 6 times, that is to say, current of the second sputtering target is at gradient decrease and current of the first sputtering targets is at gradient increase; the increase and decrease amplification may be different or same, and the time interval may also be different or same. During the whole process, the target voltage maintains unchanged at 60V bias voltage, Ti and TiC gradient film is coated for 20 min with 350 nm thickness (proportion of C increases gradually, but proportion of Ti decreases gradually).

Afterwards, while maintaining the currents and bias voltages of the second sputtering target and two first sputtering targets unchanged, on a transition layer, a nano-scale multilayer carbon film is coated, including a graphite-like and diamond-like monolayer film deposited alternately; thickness of monolayer film is 10-25 nm, total thickness thereof is 2.4 um and total duration is 8 h. Current of the second sputtering target is set as 0, pure carbon film is further deposited on the multilayer film structure for 10 min; a thickness of the pure carbon film is 100 nm. Thus, total thickness of the nano-scale multilayer carbon film is 3.0 µm; during the whole coating process, the temperature is controlled from 27° C. room temperature to 37° C. operating temperature; film base binding force is 87N and film hardness is 27.5 Gpa.

Second Embodiment

Two first sputtering targets of a magnetron sputtering coating device are graphite targets and one second sputtering target thereof is a titanium target, the radian between the second sputtering target and the first sputtering target in the sputtering device is basically at 90°, a rotary table rotates at 2.0 rpm and the matrix to be coated rotates on its axis. Before coating, firstly a matrix to be coated (or a product to be coated) is placed on a work rest of a vacuum coating chamber, a high molecular weight polyethylene joint cup is cleaned for 5 min with 99% alcohol and ultrasonic wave, the cup is further cleaned with ultra-pure water and ultrasonic wave for 5 min and then dry the cup with cold air.

At the same time, the initial magnetic field intensity is adjusted to 25 Gs with a silicon steel gasket to achieve nondestructive sputtering demands on surface of the high molecular weight polyethylene joint cup; the vacuum coating chamber is vacuumed to 1.0 mPa and then filled in 99.9% argon to clean the target material and the matrix for 5 min.

After that, sputtering is performed. During the whole sputtering process, the rotary table rotates at a constant speed and the matrix to be coated may also rotate on its axis.

Specifically, the operating air pressure of the coating chamber is controlled and maintained at 250 mPa. The magnetic field intensity of the first sputtering targets (such as graphite targets) is 150 mT; the current of the second sputtering target(s) is 2.0 A, the bias voltage is 100V. And pure Ti bottom layer is coated on the matrix for 15 min with 250 nm thickness.

Afterwards, the current of the second sputtering target is gradually decreased from 3.5 A at 0.5 A gradient change to 1.0 A for 5 times; at the same time, current of two first sputtering targets (graphite targets) is increased at 0.5 A gradient change from 0 to 3.0 A for 6 times, that is to say, current of the second sputtering target is at gradient decrease and current of the first sputtering targets is at gradient increase; the increase and decrease amplification may be different or the same, and the time interval may also be different or the same. During the whole process, the target voltage maintains unchanged at 80V bias voltage, Ti and TiC gradient film is coated for 25 min with 450 nm thickness (proportion of C increases gradually, but proportion of Ti decreases gradually).

Afterwards, while maintaining the currents and bias voltages of the second sputtering target and two first sputtering targets unchanged, on a transition layer, a nano-scale multilayer carbon film is coated, including a graphite-like and diamond-like monolayer film deposited alternately; thickness of monolayer film is 10-25 nm, total thickness thereof is 2.0 um and a total duration is 6 h. The current of the second sputtering target is set as 0, a pure carbon film on the multilayer film structure is further deposited for 15 min; thickness of pure carbon film is 150 nm. Thus, total thickness of the nano-scale multilayer carbon film is 2.75 µm; during the whole coating process, the temperature is controlled from 27° C. room temperature to 37° C. operating temperature; film base binding force is 90N and film hardness is 27.8 Gpa.

Third Embodiment

Two first sputtering targets of a magnetron sputtering coating device are graphite targets and one second sputtering target thereof is a titanium target, the radian between the second sputtering target and the first sputtering target in the sputtering device is basically at 90°, a rotary table rotates at 2.5 rpm and the matrix to be coated rotates on its axis. Before coating, firstly a matrix to be coated (or a product to be coated) is placed on a work rest of a vacuum coating chamber, a high molecular weight polyethylene joint cup is cleaned for 5 min with 99% alcohol and ultrasonic wave, the cup is further cleaned with ultra-pure water and ultrasonic wave for 5 min and then dry the cup with cold air.

At the same time, the initial magnetic field intensity is adjusted to 30 Gs with a silicon steel gasket to achieve nondestructive sputtering demands on surface of the high molecular weight polyethylene joint cup; the vacuum coating chamber is vacuumed to 1.0 mPa and then filled in 99.9% argon to clean the target material and the matrix for 5 min.

After that, sputtering is performed. During the whole sputtering process, the rotary table rotates at a constant speed and the matrix to be coated may also rotate on its axis.

Specifically, the operating air pressure of the coating chamber is controlled and maintained at 220 mPa. The magnetic field intensity of the first sputtering targets (such as graphite targets) is 110 mT; the current of the second sputtering target(s) is 3.0 A, the bias voltage is 150V. And the pure Ti bottom layer is coated on the matrix for 20 min with 300 nm thickness.

Afterwards, the current of the second sputtering target is gradually decreased from 5.0 A at 0.8 A gradient change to 1.0 A for 5 times; at the same time, current of two first sputtering targets (graphite targets) is increased at 1.0 A gradient change from 0 to 6.0 A for 6 times. That is to say, current of the second sputtering target is at gradient decrease and current of the first sputtering targets is at gradient increase; the increase and decrease amplification may be different or same, and the time interval may also be different or same. During the whole process, the target voltage maintains unchanged at 100V bias voltage, Ti and TiC gradient film is coated for 30 min with 500 nm thickness (proportion of C increases gradually, but proportion of Ti decreases gradually).

Afterwards, while maintaining the currents and bias voltages of the second sputtering target and two first sputtering targets unchanged, on a transition layer, a nano-scale multilayer carbon film is coated, including a graphite-like and diamond-like monolayer film deposited alternately; thickness of monolayer film is 10-25 nm, total thickness thereof is 3.5 um and total duration is 10 h. The current of the second sputtering target is set as 0, pure carbon film is further deposited on the multilayer film structure for 20 min; thickness of pure carbon film is 200 nm. Thus, total thickness of the nano-scale multilayer carbon film is 4.5 µm; during the whole coating process, the temperature is controlled from 27° C. room temperature to 37° C. operating temperature; film base binding force is 95N and film hardness is 28.5 Gpa.

Although the embodiments of the present invention have been shown and described, those skilled in the art can make various changes, alteration, replacement and modifications without any inventive work and without departing from the principles and spirits of the present invention. It is intended that the scope of the present invention only be limited by the appended claims.

What is claimed is:

1. An artificial joint cup, comprising:
a matrix and a nano-scale multilayer film coated on the matrix, the nano-scale multilayer film comprising:
a pure Ti bottom layer crosslinked with the matrix,
a Ti-TiC transition layer on the pure Ti bottom layer, and
a composite layer on the Ti-TiC transition layer and a pure carbon film layer on the composite layer;
wherein the composite layer is a nano-scale multilayer structure including a monolayer film with graphite-like structure and a monolayer film with diamond-like structure deposited alternately, and
wherein, in the direction from the bottom layer to the composite layer, the mass percentage of Ti in the Ti-TiC transition layer gradually decreases, and the mass percentage of C therein gradually increases.

2. The artificial joint cup according to claim 1, wherein the matrix is a high molecular weight polyethylene joint cup.

3. The artificial joint cup according to claim 1, wherein the binding force between the matrix and nano-scale multilayer film is greater than 60N.

4. The artificial joint cup according to claim 1, wherein hardness of the nano-scale multilayer film is greater than 20 Gpa.

5. The artificial joint cup according to claim 1, wherein thickness of the pure Ti bottom layer is 100-300 nm.

6. The artificial joint cup according to claim 1, wherein thickness of the Ti-TiC transition layer is 300-500 nm.

7. The artificial joint cup according to claim 1, wherein in the nano-scale multilayer structure of the composite layer including a monolayer film with graphite-like structure and a monolayer film with diamond-like structure deposited alternately, a thickness of the monolayer film is 10-25 nm and a total thickness of the composite layer is 1.5-5.0 um.

8. The artificial joint cup according to claim 1, wherein a thickness of the pure carbon film is 100 nm-200 nm.

9. A device for manufacturing an artificial joint cup comprising: a vacuum coating chamber, a sputtering target, a rotary table on a base of the vacuum coating chamber, a work rest on the rotary table, and a first rotational system driving the rotary table to rotate along a center axis of the rotary table; wherein: the sputtering target is arranged around the rotary table and vertical to the rotary table; the sputtering target comprises two first sputtering targets and one second sputtering target; the sputtering targets are positioned on a circumference homocentric with the rotary table; the arc between two the first sputtering targets is 180-240°; the second sputtering target halves the arc; the rotary table is fixedly provided with a partition passing the rotary table surface; in a direction vertical to the rotary table, both ends of the partition extend beyond both ends of the sputtering targets respectively; and the bottom of the first sputtering target is provided with a magnetic field shielding layer.

10. The device for manufacturing the above artificial joint cup according to claim 9, wherein the first sputtering targets are graphite targets and the second sputtering target is a titanium target or a tantalum target.

11. The device for manufacturing the above artificial joint cup according to claim 9, wherein the magnetic field shielding layer is a silicon steel gasket.

12. The device for manufacturing the above artificial joint cup according to claim 9, wherein the partition passes through the rotary table along a diameter of the rotary table, and a width of the partition is greater than a diameter of the rotary table.

13. The device for manufacturing the above artificial joint cup according to claim 9, wherein a distance between the partition and the circumference where the sputtering target is located is 2-10 cm.

14. The device for manufacturing the above artificial joint cup according to claim 9 or 13, wherein the sputtering targets are rectangular.

15. The device for manufacturing the above artificial joint cup according to claim 9, wherein the partition is made of titanium, aluminum, stainless steel or a combination thereof.

16. The device for manufacturing the above artificial joint cup according to claim 9, wherein the device further comprises a second rotational system driving the rotary table to rotate along the center axis of the work rest.

17. The device for manufacturing the above artificial joint cup according to claim 9, wherein the work rest is arranged on the rotary table via a support lever, and several work rests are arranged on the same support lever with intervals.

18. The device for manufacturing the above artificial joint cup according to claim 9, wherein the sputtering target is arranged on an inner wall of the vacuum coating chamber.

19. The device for manufacturing the above artificial joint cup according to claim 9, wherein: the arc between two the first sputtering targets is 180°; the sputtering target further comprises another second sputtering target; the two second sputtering targets are arranged oppositely; and the another second sputtering target is in an idle state.

20. A method for manufacturing an artificial joint cup, utilizing a device including a vacuum coating chamber, a sputtering target, a rotary table on a base of the vacuum coating chamber, a work rest on the rotary table, and a first rotational system driving the rotary table to rotate along a center axis of the rotary table, where: the sputtering target is arranged around the rotary table and vertical to the rotary table; the sputtering target comprises two first sputtering targets and one second sputtering target; the sputtering targets are positioned on a circumference homocentric with the rotary table; the arc between two the first sputtering targets is 180-240°; the second sputtering target halves the arc; the rotary table is fixedly provided with a partition passing the rotary table surface; in a direction vertical to the rotary table, both ends of the partition extend beyond both ends of the sputtering targets respectively; and the bottom of the first sputtering target is provided with a magnetic field shielding layer, the method comprising:
step 1): adjusting an initial magnetic field intensity G1 with the magnetic field shielding layer so as to meet nondestructive sputtering demands on a surface of a high molecular weight polyethylene joint cup;
step 2): controlling an initial operating air pressure of a film coating chamber at P1, and filling in 99.9% argon to clean target materials and a matrix;
step 3): controlling an operating air pressure of the film coating chamber at P2, and controlling an operating magnetic field intensity of a first sputtering target at G2; coating a pure Ti bottom layer on the matrix using the second sputtering target at an initial current I1 and a bias voltage V1, and performing sputtering for a first predetermined duration;

step 4): maintaining the bias voltage of the second sputtering target; beginning from the initial current I1, decreasing the operating current of the second sputtering target by ΔI1 at a time interval T1 until the operating current becomes a first predetermined current value; at the same time, beginning from an initial current I2, applying a bias voltage value V2 to the first sputtering target; for each second time interval T2, increasing the operating current of the first sputtering target by ΔI2 until the operating current becomes a second predetermined current value; maintaining the operating voltage of the first sputtering target and the second sputtering target, and performing sputtering for a second predetermined time duration;

step 5): maintaining the operating current of the second sputtering target at the first predetermined current value, or setting and maintaining the operating current of the second sputtering target at a third predetermined current value; maintaining the operating current of the first sputtering target at the second predetermined current value or setting and maintaining the operating current of the first sputtering targets at a fourth predetermined current value; maintaining the operating voltage of the first sputtering target and the second sputtering target, and performing sputtering for a third predetermined duration;

step 6): setting the operating current of the second sputtering target as zero; maintaining the operating current of the first sputtering target at the operating current of step 3), or setting and maintaining the operating current of the first sputtering target at a fifth predetermined current value, and performing sputtering for a fourth predetermined duration.

21. The method for manufacturing an artificial joint cup according to claim 20, wherein the initial magnetic field intensity G1 is 20-30 Gs; the initial operating air pressure P1 is 1.0 mPa; the operating air pressure P2 is controlled at 130 mPa-250 mPa; the operating magnetic field intensity G2 is 10-150 mT; the initial current I1 of the second sputtering target is 3.0-5.0 A; the bias voltage V1 is 90-150V; the ΔI1 is 0.5-1.0 A; the first predetermined current value is 0; the initial operating current I2 is 0; the ΔI2 is 0.5-1.0 A; the second predetermined current value is 3.0-6.0 A; the bias voltage V2 is 60-100V; and the first interval T1 is 3-10 min; the second interval T2 is 3-10 min.

22. The method for manufacturing an artificial joint cup according to claim 20, wherein the first predetermined duration is 10-30 min.

23. The method for manufacturing an artificial joint cup according to claim 20, wherein the second predetermined duration is 10-30 min.

24. The method for manufacturing an artificial joint cup according to claim 20, wherein the third predetermined duration is 5-10 h.

25. The method for manufacturing an artificial joint cup according to claim 20, wherein the fourth predetermined duration is 10-20 min.

26. The method for manufacturing an artificial joint cup according to claim 20, wherein the temperature during the whole film coating process is controlled at 30-40° C.

27. The method for manufacturing an artificial joint cup according to claim 21, wherein the temperature during the whole film coating process is controlled at 30-40° C.

* * * * *